United States Patent [19] [11] 4,120,846
Spivack et al. [45] Oct. 17, 1978

[54] BENZOYLOXYBENZOATES AND COMPOSITIONS STABILIZED THEREWITH

[75] Inventors: John D. Spivack, Spring Valley; John J. Luzzi, Carmel, both of N.Y.

[73] Assignee: Ciba-Geigy Corporation, Ardsley, N.Y.

[21] Appl. No.: 835,760

[22] Filed: Sep. 22, 1977

Related U.S. Application Data

[60] Division of Ser. No. 563,251, Mar. 28, 1975, Pat. No. 4,051,104, which is a continuation of Ser. No. 318,324, Dec. 26, 1972, abandoned.

[51] Int. Cl.$^2$ .................. C07C 153/11; C08K 9/04
[52] U.S. Cl. .................. 260/45.85 B; 260/455 R; 260/45.85 H; 260/45.85 P
[58] Field of Search ............ 260/455 R, 45.85 B, 260/45.85 H, 45.85 P

[56] References Cited
U.S. PATENT DOCUMENTS 2,983,708  5/1961  Lappin ........................ 260/45.85 B
4,051,104  9/1977  Spivack et al. ............... 260/45.85 B Primary Examiner—Lewis Gotts
Assistant Examiner—Robert C. Whittenbaugh
Attorney, Agent, or Firm—Vincent J. Cavalieri

[57] ABSTRACT

Benzoyloxybenzoates having the formula

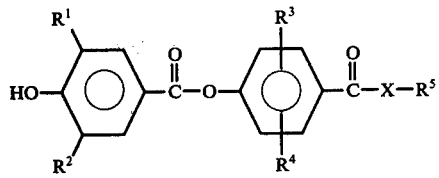

wherein
$R^1$, $R^2$, $R^3$ and $R^4$ are lower alkyl or cycloalkyl,
X is oxygen or sulfur, and
$R^5$ is alkyl, aryl, alkaryl or hydrogen are useful as stabilizers of organic materials such as polyolefins.

5 Claims, No Drawings

BENZOYLOXYBENZOATES AND COMPOSITIONS STABILIZED THEREWITH

This is a Divisional of application Ser. No. 563,251 filed on Mar. 28, 1975 now U.S. Pat. No. 4,051,104, which is a Cont. of Ser. No. 318,324, filed on Dec. 26, 1972, now abandoned.

BACKGROUND OF THE INVENTION

Polymeric materials have one important deficiency which must be overcome before they can be used in various commercial applications. This deficiency is the susceptibility to oxidative and actinic degradation. Many varieties of compounds have been known to be useful as stabilizers of various polymers, but all of then have certain deficiencies which limits the usefulness of such stabilizers. Thus, one class of stabilizers disclosed in the prior art that is related to the compounds of this invention is hindered hydroxybenzoates disclosed in U.S. Pat. Nos. 3,029,276; 3,112,338; 3,206,431 and 3,502,613.

Most of the compounds disclosed in said patents are various esters of 3,5-dialkyl-4-hydroxybenzoic acids while the benzoyloxybenzoates of this invention are esters of 4-(3,5-dialkyl-4-hydroxybenzoyloxy)-mono or dialkylbenzoic acid. The most closely related compound in the prior art is ethyl-4-(3,5-di-t-butyl-4-hydroxybenzoyloxy) benzoate disclosed in U.S. Pat. No. 3,206,431. In this compound the phenyl ring in the benzoate group is completely unsubstituted while the corresponding group in the compounds of this invention has two alkyl substituents. The important difference in the properties between the prior art compounds discussed above and the benzoyloxybenzoates is the improved thermal stability of the instant compounds. This is a very important feature because the polymer substrates which are stabilized with such compounds are subjected to high temperature processing during the various manufacturing stages. Compounds which are not thermally stable will decompose during processing which will result in decreased stabilization effectiveness during the life of the polymer and also may introduce discoloration.

DETAILED DISCLOSURE

This invention relates to hindered benzoyloxybenzoate compounds and organic compositions stabilized therewith. More specifically, these compounds are useful as stabilizers of organic materials which are subject to thermal, oxidative and ultraviolet light degradation. The novel benzoyloxybenzoate compounds can be represented by the formula

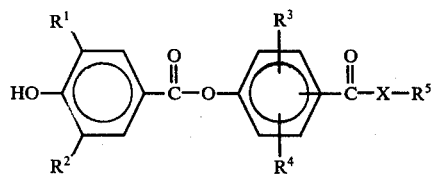

wherein
$R^1$, $R^2$, $R^3$ and $R^4$ are (lower)alkyl or (lower) cycloalkyl groups,
$R^5$ is an alkyl group having up to 30 carbon atoms, aryl groups having up to 12 carbon atoms or alkyl substituted aryl groups having up to 24 carbon atoms, and hydrogen and
X is oxygen or sulfur.

Each of the groups $R^1$, $R^2$, $R^3$ and $R^4$ can be the same or different (lower)alkyl groups having from 1 to 8 carbon atoms, namely, n-propyl, isopropyl, n-butyl, sec-butyl, tert-butyl, sec-amyl, tert-amyl, n-hexyl, sec-hexyl, sec-octyl, tert-octyl and the like. These groups can also be (lower)cycloalkyl groups having 4 to 8 carbon atoms, such as cyclobutyl, cyclopentyl, cyclohexyl or cyclooctyl groups.

Although groups $R^1$, $R^2$, $R^3$ and $R^4$ can be any (lower)alkyl groups stated above, it is preferable that $R^1$ and $R^2$ groups be secondary or tertiary alkyl groups having from 3 to 8 carbon atoms and most preferably tertiary alkyl. Tertiary-butyl group is found to be very effective. The above formula indicates that $R^3$ and $R^4$ can be substituted on any of the four open positions in the benzene ring but preferably both groups are ortho to the benzoic acid moiety. The formula also indicates that the group

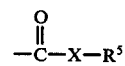

can be bonded to the phenyl ring in either meta or para position in relation to the hindered hydroxybenzoic acid moiety.

The group $R^5$ is an alkyl group having up to 30 carbon atoms and preferably up to 18 carbon atoms. Illustrative examples of such groups are methyl, ethyl, butyl, hexyl, octyl, dodecyl, hexadecyl, octadecyl, tetracosyl and the like. This group can also be an aryl group such as phenyl or naphthyl or an alkyl substituted aryl group having up to about 20 carbon atoms. Illustrative examples of the alkyl substituted groups are tolyl, xylyl, mesitylyl, ethylbenzyl, 1,3,5-triethylbenzyl, 1,1,3,3-tetramethylbutylphenyl, di-t-butylphenyl, octylphenyl, dodecylphenyl and the like.

Following are illustrative examples of the compounds of this invention:
p-(1,1,3,3-tetramethylbutyl)phenyl-4-(3,5-di-t-butyl-4-hydroxybenzoyloxy)-3,5-di-t-butylbenzoate
p-(1,1,3,3-tetramethylbutyl)phenyl-4-(3,5-di-t-butyl-4-hydroxybenzoyloxy)-3,5-di-t-butylbenzoate
m-methylphenyl-4-(3,5-di-t-butyl-4-hydroxybenzoyloxy)-3,5-di-t-butylbenzoate
n-octyl-4-(3,5-di-t-butyl-4-hydroxybenzoyloxy)-3,5-di-t-butylthiobenzoate
(2,4-di-t-butyl)phenyl-4-(3,5-di-t-butyl-4-hydroxybenzoyloxy)-3,5-di-t-butylbenzoate
n-octadecyl-4-(3,5-di-t-butyl-4-hydroxybenzoyloxy)-3,5-di-t-butylbenzoate
methyl-4-(3,5-di-tert.butyl-4-hydroxybenzolyloxy)-3,5-di-tert.butylbenzoate
2,2-dimethylpropyl-4-(3,5-di-t-butyl-4-hydroxybenzoyloxy)-3,5-di-t-butylbenzoate
n-octyl-4-(3,5-di-t-butyl-4-hydroxybenzoyloxy)-3,5-di-t-butylbenzoate
n-dodecyl-4-(3,5-di-t-butyl-4-hydroxybenzoyloxy)-3,5-di-t-butylbenzoate
2-ethylhexyl-(3,5-di-tert.butyl-4-hydroxybenzoyloxy)-3,5-di-tert.butylbenzoate
methyl-4-(3,5-di-tert.butyl-4-hydroxybenzoyloxy)-3,5-dimethylbenzoate The compounds of this invention when $R^1$ and $R^2$ are different from $R^3$ and $R^4$ can be prepared by reacting a hindered phenolic acid chloride such as 3,5-di-tertbutyl-4-hydroxybenzoylchloride with an appropriate alkyl substituted benzoate or thiobenzoate at a temperature of from about 50° to 200° C. Compounds where $R^1$ and $R^2$ are the same as $R^3$ and $R^4$ can be prepared by reacting two moles of a dialkyl substituted hydroxybenzoyl halide with one mole of a base to yield an intermediate compound which is (di-alkyl substituted hydroxybenzoyloxy)-dialkyl benzoyl halide which in turn is reacted with an alcohol or a mercaptan to give the desired product. The basic materials which can be employed are trialkyl amines such as triethyl amine, tripropyl amine, triisopropyl amine, tributyl amine, triamyl amine, sodium or potassium hydroxide, sodium or potassium carbonates or other similar proton acceptors. Both reactions mentioned above can be carried out neat or in a non-reactive solvent such as a hydrocarbon as for example, hexane, cyclohexane, heptane, non-reactive chlorinated hydrocarbon, mineral oil, and preferably benzene or toluene.

Compounds of the above formula where $R^5$ is hydrogen are conveniently made by hydrolysis in known fashion of the (dialkylsubstituted hydroxybenzoyloxy)-dialkylbenzoyl halide.

The preparation of these compounds is further illustrated in greater detail in the examples below.

EXAMPLE 1

Preparation of 4-(3,5-di-t-butyl-4-hydroxybenzoyloxy)-3,5-di-t-butylbenzoyl chloride To 445 ml. of a toluene solution containing 107.2 grams of 3,5-di-t-butyl-4-hydroxybenzoyl chloride (0.40 moles) cooled to 10° C. was added 24.4 grams (0.24 moles) of triethylamine over a period 20 minutes at 10° to 15° C. The turbid reaction mixture was maintained at room temperature for about 19 hours and then heated at 80° C. for 1 hour. The precipitate was removed by filtration and washed with a little toluene. The clear filtrate was concentrated in vacuo at 40° to 50° C. at 20 mm. Hg. pressure and kept at this same temperature for 45 minutes at 20 mm. Hg. pressure to yield 105 grams of residue. The residue was triturated with 200 ml. of warm petroleum ether, and the slurry cooled. The white crystals were filtered yielding 70 grams of the product. After recrystallization from heptane and acetonitrile and drying at 95° C. for 5 hours at 0.1 mm Hg. pressure the melting point of the product was 210°–213° C.

EXAMPLE 1a

Preparation of 4-(3,5-di-tert-butyl-4-hydroxybenzoyloxy)-3,5-di-tert-butylbenzoic Acid 25.2 g of triethylamine was added dropwise to 505 ml of 0.99 molar toluene solution of 3,5-di-t-butyl-4-hydroxybenzoyl chloride at 10° to 15° C. over a period of 15 minutes in a nitrogen atmosphere. The reaction was allowed to stir for an additional 2¼ hours at room temperature (25° C.). The precipitated triethylamine hydrochloride was filtered and washed with a little toluene.

450 ml of 2N sodium hydroxide were added to the toluene filtrate at room temperature and gradually heated to reflux. The reaction was heated at reflux for 4½ hours. The reaction mixture was cooled to 0° to 5° C. by an ice-water bath whereupon a thick precipitate formed. 70 ml of concentrated aqueous hydrochloric acid was gradually added dropwise with cooling at 30° C. 150 ml of ether was added with stirring to the reaction mixture at 20° to 25° C. The aqueous phase was separated and the organic phase washed with two 100 ml portions of water. The separated organic phase was then dried over anhydrous sodium sulfate. The residue was isolated from the organic phase by evaporation of the solvent initially at about 20 mm Hg. pressure and finally at 0.5 mm. Hg.

The glassy residue was ground in a mortar and then triturated with stirring at reflux with a 150 ml portion of petroleum ether in a 3-neck flask. The slurry was then cooled to room temperature, the solid isolated by filtration and triturated once again. The petroleum filtrate from the second trituration was colorless. After drying in the vacuum oven overnight at 40° C. at 1 mm. Hg. pressure, the product was isolated as a white powder. The product melts at about 301° to 306° C., the melting range depends on the heating rate.

EXAMPLE 2

Preparation of p-(1,1,3,3-tetramethylbutyl) phenyl-4-(3,5-di-t-butyl-4-hydroxybenzoyloxy)-3,5-di-t-butylbenzoate 3.0 grams of triethylamine was added dropwise over a period of ten minutes at 25° to 35° C. to a solution of 6.2 grams of p-(1,1,3,3-tetramethylbutyl)phenol (0.03 moles) and 15.0 grams of 4-(3,5-di-t-butyl-4-hydroxybenzoyloxy)-3,5-di-t-butylbenzoyl chloride in 100 ml. of toluene. The reaction mixture was stirred at room temperature for about 5 hours and then heated at reflux for 30 minutes. The precipitate was filtered, the toluene filtrate was washed with water and dried over a sodium sulfate. The dry toluene solution was concentrated at reduced pressure to isolate 20.1 grams of the product. After recrystallization from acetonitrile the product was obtained as white crystals (15.5 grams) melting at 174°–176° C.

EXAMPLE 3

Preparation of phenyl 4-(3,5-di-t-butyl-4-hydroxybenzoyloxy)-3,5-di-t-butyl benzoate This compound was prepared by substantially the same procedure as in Example 2 by reacting phenol with 4-(3,5-di-t-butyl-4-hydroxybenzoyloxy)-3,5-di-t-butylbenzoyl chloride. After recrystallization from acetonitrile, 10.1 grams of purified product melting at 202°–204° C. was obtained.

EXAMPLE 4

Preparation of m-methylphenyl-4-(3,5-di-t-butyl-4-hydroxybenzoyloxy)-3,5-di-t-butylbenzoate This compound was prepared according to the procedure of Example 2 by reacting m-cresol with the same benzoyl chloride. After crystallization from acetonitrile, 9.8 g of white crystals were obtained (m.p. 200° to 202° C.).

Following the same procedure m-methylphenyl-4-(3,5-diisopropyl-4-hydroxybenzoyloxy)-3,5-diisopropyl-benzoate is prepared from m-cresol and 4-(3,5-diisopropyl-4-hydroxybenzoyloxy)-3,5-diisopropylbenzoyl chloride.

EXAMPLE 5

Preparation of
(2,4-di-t-butyl)phenyl-4-(3,5-di-t-butyl-4-hydroxybenzoyloxy)-3,5-di-t-butylbenzoate 10.3 g of 2,4-di-t-butylphenol, 11.1 g. of triethylamine, 50 ml. of toluene were charged into a 300 ml. 3 neck flask equipped with stirrer, thermometer, condenser, drying tube, dropping funnel and nitrogen inlet. 26.85 of 3,5-di-t-butyl-4-hydroxybenzoyl chloride was added dropwise over a 15 minute period. The temperature during the addition and for one half hour thereafter was maintained between 10°–15° C. The reaction was then permitted to stand at room temperature overnight.

The next day the precipitate was removed by filtration. The mother liquor was placed in a separatory funnel and worked up with ether and distilled water. The ether layer was successively washed with 200 ml. normal NAOH and distilled water. The ether layer was then dried over sodium sulfate. After standing overnight, the solvent was stripped and the residue heated a short time to 50° C. under a good vacuum yielding the product. This crude was then triturated with cold methanol and recrystallized from heptane. After drying over $P_2O_5$ at reduced pressure, 6.4 g. of product was recovered (m.p. 251°–254° C.).

EXAMPLE 6

Preparation of
n-octyl-4-(3,5-di-t-butyl-4-hydroxybenzoyloxy)-3,5-di-t-butylthiobenzoate Following the procedure of Example 5, n-octanol was reacted with the same benzoyl chloride to yield the product. After recrystallization from methanol and drying over $P_2O_5$ under reduced pressure it melted at 129°–132° C.

EXAMPLE 7

Preparation of
methyl-4-(3,5-di-t-butyl-4-hydroxybenzoyloxy)-3,5-di-t-butylbenzoate Following the procedure of Example 5, methanol is reacted with the same benzoyl chloride yielding the product which, after recrystallization, had a melting point of 206°–209° C.

EXAMPLE 8

Preparation of
(2,4-di-t-butyl)phenyl-4-(3,5-di-t-butyl-4-hydroxybenzoyloxy)-3,5-di-t-butylbenzoate 7.2 grams of 2,4-di-t-butylphenol (0.035 moles) was dissolved in 200 ml. of dried toluene. To the toluene solution at 20° C. was then added 17.6 grams of 4-(3,5-di-t-butyl-4-hydroxybenzoyloxy)-3,5-di-t-butylbenzoyl chloride (0.035 moles) and 4.1 grams of triethylamine (0.040 moles). The solution was gradually heated to 90° C. and maintained at 90° to 95° C. for 4 to 5 hours. The reaction mixture was cooled to room temperature, the precipitate filtered off and the filtrate washed successively with aqueous saturated sodium bicarbonate solution and with water. The toluene solution was then dried over anhydrous sodium sulfate and the toluene evaporated by distillation at reduced pressure, yielding about 24 grams of product. The product was crystallized by trituration with nitromethane the crystals being recrystallized from isopropanol and finally from n-heptane. The resulting white crystals melted at 249°–251° C.

EXAMPLE 9

Preparation of
n-octadecyl-4-(3,5-di-t-butyl-4-hydroxybenzoyloxy)-3,5-di-t-butylbenzoate 10.0 grams of 4-(3,5-di-t-butyl-4-hydroxybenzoyloxy)-3,5-di-t-butylbenzoyl chloride (0.02 moles) 5.4 grams of n-octadecanol (0.02 moles) and 2.0 grams of triethylamine were stirred together in 100 ml. of benzene at room temperature for 2 hours and then heated for 1 hour at 60° to 70° C. The reaction mixture was cooled to room temperature and the precipitate filtered. The benzene solution was washed with water and dried over sodium sulfate. The benzene solution was then concentrated at reduced pressure yielding about 15 grams of the product. The product was crystallized twice from isopropanol yielding white crystals melting at 75° to 76° C.

EXAMPLE 10

Preparation of
Methyl-4-(3,5-di-tert.butyl-4-hydroxybenzoyloxy)-3,5-di-tert.butylbenzoate (a) Preparation of 3,5-di-tert.butyl-4-hydroxybenzoyl Chloride - After flushing the reaction vessel with nitrogen, 369 g. of 3,5-di-t-butyl-4-hydroxybenzoic acid dissolved in 1.5 l. of toluene and 2.9 ml. of dimethylformamide were placed into the vessel. To this mixture 211 g. of thionyl chloride was added dropwise at room temperature.

After the addition was complete, the reaction was heated at 55° to 60° C. for 3 hours and finally at 80° to 85° C. for 1 hour. The solution was slightly turbid and was clarified by filtration. The clear filtrate was concentrated by distillation at 15 mm Hg. pressure at about 50° C. and finally at 1 mm Hg. while heating at 98° to 105° C. This yielded 375 g. of the acid chloride which was dissolved in 2.0 l. of toluene to give a 0.70 molar solution.

(b) Preparation of above named benzoate - In a nitrogen atmosphere 5.05 g. of triethylamine was added dropwise to 143 ml of the acid chloride solution over a period of ten minutes at room temperature. The reaction mixture was stirred at room temperature for two hours. 3.46 g. of absolute methanol was added dropwise at room temperature over a period of ten minutes, the temperature rising slowly to 30° C. The reaction was held at 30° C. for 45 minutes. The reaction mixture was then raised to reflux and heated at this temperature for 2.5 hours. The reaction mixture was then cooled to room temperature and filtered. The toluene filtrate was washed once with 50 ml of water, then twice with 50 ml of 10% sodium carbonate, and finally twice with 50 ml of water. The organic phase was separated and the toluene removed by distillation at 50° to 60° C. at water aspirator pressures yielding 22.2 grams of viscous residue. 75 ml of isopropanol was added to the reaction product and heated at reflux for 30 minutes to give a dispersion of crystalline material. The dispersion was cooled with an ice- water bath and held under these conditions for 1 hour. The crystalline product was filtered and washed with two 50 ml portions of ice cold isopropanol. The filter cake was then dried in the vacuum oven at 60° C. and about 100 mm. Hg. pressure.

19.5 gr. of white crystalline product (m.p. 207°–210° C.) was obtained.

EXAMPLE 11

Preparation of 2,2-Dimethylpropyl-4'-(3,5-di-t-butyl-4-hydroxybenzoyloxy)-3,5-di-t-butylbenzoate Following the procedure of Example 10 except for employing neopentyl alcohol in place of methanol, the above named product having the melting point of 179°–181° C. was obtained.

EXAMPLE 12

Preparation of n-octyl-4-(3,5-di-t-butyl-4-hydroxybenzoyloxy)-3,5-di-t-butylbenzoate To 286 ml. of a 0.7 molar solution of 3,5-di-t-butyl-4-hydroxybenzoyl chloride, 10.1 g. of triethylamine was added dropwise at 10° to 15° C. over a period of ten minutes. The reaction mixture was then held at room temperature for 2 hours. 14.3 g. of n-octanol was added rapidly at room temperature followed by the dropwise addition of 10.1 g. of triethylamine over a period of seven minutes at 25°. The reactants were then stirred at room temperature overnight. The precipitate was filtered, washed with a little toluene, the toluene washing being added to the filtrate. The toluene solution was washed with water, dried over anhydrous sodium sulfate and concentrated in vacuo yielding 61.9 g. of product as a viscous liquid. The product was isolated as white crystals (m.p. 94°–97° C.) by crystallization from acetonitrile.

EXAMPLE 13

Preparation of n-dodecyl-4-(3,5-di-t-butyl-4-hydroxybenzoyloxy)-3,5-di-t-butylbenzoate This compound was made in substantially the same procedure as described in Example 12 except for substituting n-dodecanol for n-octanol. The product was isolated as white crystals (m.p. 53°–56° C.) by crystallization from methanol.

EXAMPLE 14

Preparation of 2-ethylhexyl-4'-(3,5-di-tert.butyl-4-hydroxybenzoyloxy)-3',5'-di-tert.butylbenzoate Following substantially the procedure of Example 10 except for employing 0.5 mole of 2-ethylhexanol for each mole of 3,5-di-tert.butyl-4-hydroxybenzoyl chloride the above named product was obtained. This compound had a melting point of 108°–110° C.

EXAMPLE 15

Preparation of methyl 4-(3,5-di-tert.butyl-4-hydroxybenzoyloxy)-3,5-dimethylbenzoate 5.4 grams of methyl 3,5-dimethyl-4-hydroxybenzoate (0.03 moles) is dissolved in 30.8 ml of a 0.99 molar toluene solution of 3,5-di-tert.butyl-4-hydroxybenzoyl chloride and heated at reflux (119° C.) for 2 and ½ hours the evolved hydrogen chloride being swept out of the reaction by a stream of nitrogen. After this period, sufficient toluene (ca 5 to 10 ml) is removed so as to raise the reaction temperature to 128° to 132° C. and heating continued under a nitrogen atmosphere for an additional 2 hours. After cooling to room temperature, the reaction mixture is dissolved in 100 ml of toluene and successively washed with 2N aqueous sodium hydroxide and then with water until the wash waters were neutral. The washed toluene solution was dried over anhydrous sodium sulfate, filtered and the solvent removed by distillation under vacuum at 50°–60° C. initially at about 20 mm Hg. and finally at 0.3 mm Hg. The resulting residue is ground to a powder and triturated with boiling hexane. The ice-cold slurry is then filtered to yield light yellow crystals, which are then recrystallized from a solvent mixture of 50 ml of toluene and 40 ml of n-hexane. The crystals were filtered, washed with same solvent mixture and dried in vacuum. Methyl-4-(3,5-di-tert.butyl-4-hydroxybenzoyloxy)-3,5-dimethylbenzoate is then obtained as white crystals melting at 180°–182° C.

The benzoyloxybenzoates of this invention are stabilizers of organic material normally subject to thermal, oxidative or actinic light deterioration. Materials which are thus stabilized include synthetic organic polymeric substances such as vinyl resins formed from the polymerization of vinyl halides or from the copolymerization of vinyl halides with unsaturated polymerizable compounds, e.g., vinyl esters, α,β-unsaturated ketones, α,β-unsaturated aldehydes and unsaturated hydrocarbons such as butadienes and styrene; poly-α-olefins such as polyethylene, polypropylene, polybutylene including copolymers of α-olefins; dienes such as polybutadiene, polyisoprene, and the like, including copolymers with other monomers; polyurethanes and polyamides such as polyhexamethylene adipamide and polycaprolactam; polyesters such as polyethylene terephthalates; polycarbonates; polyacetals such as polyethylene terephthalate polyacetal; polystyrene, polyethyleneoxide; and copolymers such as those of high impact polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethylene glycol, octaethyleneglycol, dibutyleneglycol, dipropyleneglycol and the like.

Of particular importance are polyolefins and especially polypropylene because these benzoyloxybenzoates are particularly effective as UV stabilizers in polypropylene.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, or the like into films, fibers, filaments, hollow spheres and the like. The heat stabilizing properties of these compounds advantageously stabilize the polymer against degradation during such processing at the high temperature generally encountered. The stabilizers can also be dissolved in suitable solvents and sprayed on the surface of films, fabrics, filaments or the like to provide effective stabilization.

These compounds can also be used in combination with other additives such as antioxidants, sulfur-containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, carbon black, accelerators and other chemicals used in rubber compounding, plasticizers, color stabilizers, di- and tri-alkyl- and -alkylphenyl-phosphites, heat stabilizers, ultraviolet light stabilizers, antiozonants, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in coination with the stabilizers of this invention:

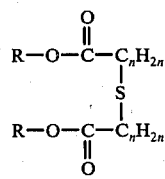

wherein R is an alkyl group having from 6 to 24 carbon atoms; and n is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention are also effective as thermal stabilizers, if the processing of the polymer is carried out at high temperatures it is advantageous to incorporate additional antioxidants.

The antioxidant compounds that can be employed are various hindered phenolic compounds which can be illustrated by the compounds listed below:

di-n-octadecyl(3-t-butyl-4-hydroxy-5-methylbenzyl)-malonate
2,6-di-t-butylphenol
2,2'-methylene-bis(6-t-butyl-4-methylphenol)
2,6-di-t-butylhydroquinone
octadecyl-(3,5-di-t-butyl-4-hydroxybenzylthio)acetate
1,1,3-tris(3-t-butyl-6-methyl-4-hydroxyphenyl)-butane
1,4-bis(3,5-di-t-butyl-4-hydroxybenzyl)-2,3,5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl β-(3,5-di-t-butyl-4-hydroxyphenyl) propionate
n-octadecyl-3,5-di-t-butyl-4-hydroxybenzoate
2-(n-octylthio)ethyl-3,5-di-t-butyl-4-hydroxybenzoate
stearamido N,N-bis-{ethylene 3-(3,5-di-t-butyl-4-hydroxyphenyl)propionate}
1,2-propylene glycol bis-{3-(3,5-di-t-butyl-4-hydroxyphenyl)propionate}
pentaerithritol tetrakis-{3-(3,5-di-t-butyl-4-hydroxyphenyl)propionate}
dioctadecyl-3,5-di-t-butyl-4-hydroxybenzyl-phosphonate
di-n-octadecyl-1-(3,5-di-t-butyl-4-hydroxyphenyl)-ethanephosphonate The above antioxidants have been listed only for the purpose of illustration and it is important to note that any other antioxidant can be employed with the same improved results. The above exemplified antioxidants are disclosed in greater detail in the following patents: Netherlands Pat. No. 67/1119, issued Feb. 19, 1968; Netherlands Pat. No. 68/03498 issued Sept. 18, 1968; U.S. Pat. Nos. 3,255,191; 3,330,859; 3,281,505; 3,285,855; 3,364,250; 3,368,997 and 3,357,944.

To further illustrate the present invention additional examples are presented without introducing any limitations to the description of the invention.

Outdoor Light Exposure Test

15 Denier Oriented Monofilaments

The additives are solvent blended (e.g., methylene chloride) with powdered polypropylene (Hercules Profax 6501). The solvent is then removed at room temperature in a vacuum oven with a slight air bleed. The dry mixture is melt-extruded at 450° F. and pelletized. The pellets are reextruded through a monofilament die, melt spun and hot oriented 4:1 by means of a set of cold and hot Godet rolls to give 15 denier (nominal) monofilaments.

The test results reported in Examples of Table I show the percentage of retention of the original tenacity by a fiber after having been exposed to the indicated number of Kilolangleys (Kly) of Florida exposure. A Langley is a measure of energy accumulated by the fiber.

Table I shows the results of the above described outdoor test indicating amounts of the additives present. Thus, in the Additives column is given the percentage of the compound prepared in the indicated Example which is present in the polypropylene composition in addition to the additives present in the base formulation. The remaining two columns show the number of Kilolangleys of exposure in Florida at the indicated percentage of retention of the original tenacity to which the fibers have been subjected.

TABLE 1

Outdoor Exposure of 15 Denier
Polypropylene Monofilaments in Florida

Base Formulation: 0.2% IRGANOX 1093
0.1% Calcium Stearate

| Ex. No. | Additives | Kiloangleys to | |
|---|---|---|---|
| | | 30% Retention of Tenacity | 50% Retention of Tenacity |
| 16 | Base Formulation | 41 | 36 |
| 17 | 0.25% Example 5 | 79 | 61 |
| 18 | 0.05% Example 5 | 113 | 87 |
| 19 | 0.75% Example 5 | 125 | 96 |
| 20 | 0.25% Example 5 + 0.25% TIN 327 | 105 | 86 |
| 21 | 0.25% Example 9 | 79 | 63 |
| 22 | 0.50% Example 9 | 121 | 90 |

TABLE 1-continued

Outdoor Exposure of 15 Denier
Polypropylene Monofilaments in Florida

Base Formulation: 0.2% IRGANOX 1093
0.1% Calcium Stearate

| | | Kiloangleys to | |
|---|---|---|---|
| Ex. No. | Additives | 30% Retention of Tenacity | 50% Retention of Tenacity |
| 23 | 0.25% Example 9 + 0.25% TIN 327 | 92 | 79 |
| 24 | 0.50% Example 7 | 125 | 106 |
| 25 | 0.25% Example 2 | 58 | 51 |
| 26 | 0.50% Example 2 | 68 | 61 |
| 27 | 0.75% Example 2 | 86 | 76 |
| 28 | 0.25% Example 2 + 0.25% TIN 327 | 83 | 75 |

*IRGANOX 1093 is an antioxidant dioctadecyl3,5-di-t-butyl-4-hydroxybenzylphosphonate
**TINUVIN 327 is a UV absorber 2(2'-hydroxy-3',5'-di-t-butyl-phenyl)-5-chlorobenzotriazole Proportionately good stabilization is obtained when in the compositions of Table I the compounds of this invention are present in the concentrations of 0.1% and 1%.

EXAMPLE 29

Pellets (500 g) of unstabilized nylon-6,6 (Zytel 101, DuPont) are placed in a Kitchen Aid Mixer. With mixing a solution of 0.5% (based on the weight of nylon) of n-tetracosyl-4-(3,5-dimethyl-4-hydroxybenzoyloxy)-3-methylbenzoate in 20 ml of methylene chloride is added slowly. Sodium hypophosphite (0.5 gm. 0.1%) is dissolved in 20 ml of water and added slowly with mixing to the nylon pellets after the antioxidant solution has been added and most of the methylene chloride has evaporated. The stabilized pellets are dried at 80° C. at <1mm for 4 hours.

The polyamide formulation is extruded at 600° F. through at ¼ inch die into a rod which is water cooled and chopped into pellets. A ¾ inch Brabender extruder, equipped with a nylon screw, is used. The pellets are dried at 80° C. at <1mm for 4 hours.

The dried pellets are reextruded into 5 mil (nominal) monofilament fiber which is subsequently oriented (4:1). The oriented fibers are exposed to outdoor weathering (direct and under glass) and tensile measurement is made periodically. The sample is considered to have failed when it loses 50% of its original tenacity. The sample stabilized with the above noted benzoate retained tensile strength for a much longer period than the unstabilized sample.

EXAMPLE 30

Unstabilized high impact polystyrene resin is dry blended with 0.01% by weight of the resin of (2-t-butyl-phenyl)-4-(3,5-dimethyl-4-hydroxybenzoyloxy)-3,5-di-t-butyl-benzoate. The resin is then extrusion compounded on a 1 inch 24/1=L/D extruder, melt temperature 500° F. and then pressed for 7 minutes at a temperature of 163° C. and a pressure of 2000 psi into a sheet of uniform thickness of 100 mil. The sheets are then cut into plaques of 2 inch × 2 inch. The plaques are then exposed in a FS/BL exposure device and color measurements made periodically using a Hunter Color Difference Meter Model D25. The polystyrene samples stabilized with the above benzoate developed the undesirable yellow discoloration substantially later after such discoloration occured in the unstabilized samples.

EXAMPLE 31

Unstabilized linear polyethylene is solvent blended in methylene chloride with 0.5% by weight of the substrate of n-octyl-4-(3,5-di-t-butyl-4-hydroxybenzoyloxy)-3,5-di-t-butylthiobenzoate and then vacuum dried. The resin is then extruded at 450° F. as described in Example 30. Thereafter, the test procedure of Example 30 is followed and the light stability of the samples determined. Polyethylene stabilized with the above benzoate is found to be much more stable than the unstabilized polyethylene or the polyethylene stabilized only with an antioxidant.

EXAMPLE 32

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for one half hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40°-45° C.

The dried rubber (25 g) is heated under nitrogen at 125° C. in a Brabender mixer and to this is added with mixing 0.25 g (0.5%) of methyl-4-(3,5-di-t-butyl-4-hydroxybenzoyloxy)-3,5-di-t-butylbenzoate. The composition is mixed for 5 minutes after which it is cooled and compression molded at 125° C. into 5 × 0.025 inch plaques.

The plaques are exposed to a xenon arc weatherometer and the color measurement (L-b) is made after 45, 125 and 290 hours. The samples stabilized with the above benzoate is found to be much more light stable than the unstabilized samples.

EXAMPLE 33

To 50 g of polyacetal resin containing 0.1% of an acid scavenger, dicyandiamide, is added 0.2% by weight of n-dodecyl-4-(3,5-di-t-butyl-4-hydroxybenzoyloxy)-3,5-di-t-butylbenzoate, and milled for 7 minutes at 200° C. in a Brabender Plasti-recorder. The milled formulation is subsequently pressed into a 40 mil sheet at 215° C. at 350 psi for 90 seconds then cooled quickly in a cold press at 350 psi. The stabilized sheets are then remolded for 2 minutes at contact pressure and for 3 minutes at 300 psi at 215° C. to give plaques 1½ inch × 2¼ inch × 125 mil. Thereafter, the testing procedure of Example 30 is followed to determine the light stability of the samples. The stabilized samples are found to be much more stable than the unstabilized samples.

EXAMPLE 34

Unstabilized thoroughly dried polyethylene terephthalate chips are dry blended with 1.0% of 2-ethyhexyl-4-(3,5-di-t-butyl-4-hydroxybenzoyloxy)-3,5- di-t-butylbenzoate. 60/10 denier multifilament is is melt spun at a melt temperature of 290° C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

We claim:

1. A benzoyloxybenzoate having the structure

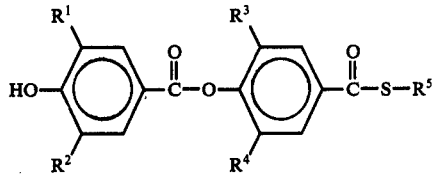

wherein
$R^1$, $R^2$, $R^3$, and $R^4$ are tert-butyl groups,
$R^5$ is alkyl group having up to 30 carbon atoms, phenyl or alkyl substituted phenyl having up to 24 carbon atoms.
2. The compound of claim 1 wherein $R^5$ is alkyl of 1 to 18 carbon atoms.
3. The compounds according to claim 1 wherein $R^5$ is alkyl substituted phenyl.
4. A composition of matter stabilized against degradation which comprises an organic material subject to oxidative and ultraviolet light degradation and a compound of claim 1.
5. A composition of claim 4 wherein the organic material is polypropylene.

* * * * *